Nov. 2, 1976 D. L. ARMSTRONG Plant Pat. 3,972
ROSE PLANT
Filed Nov. 18, 1975
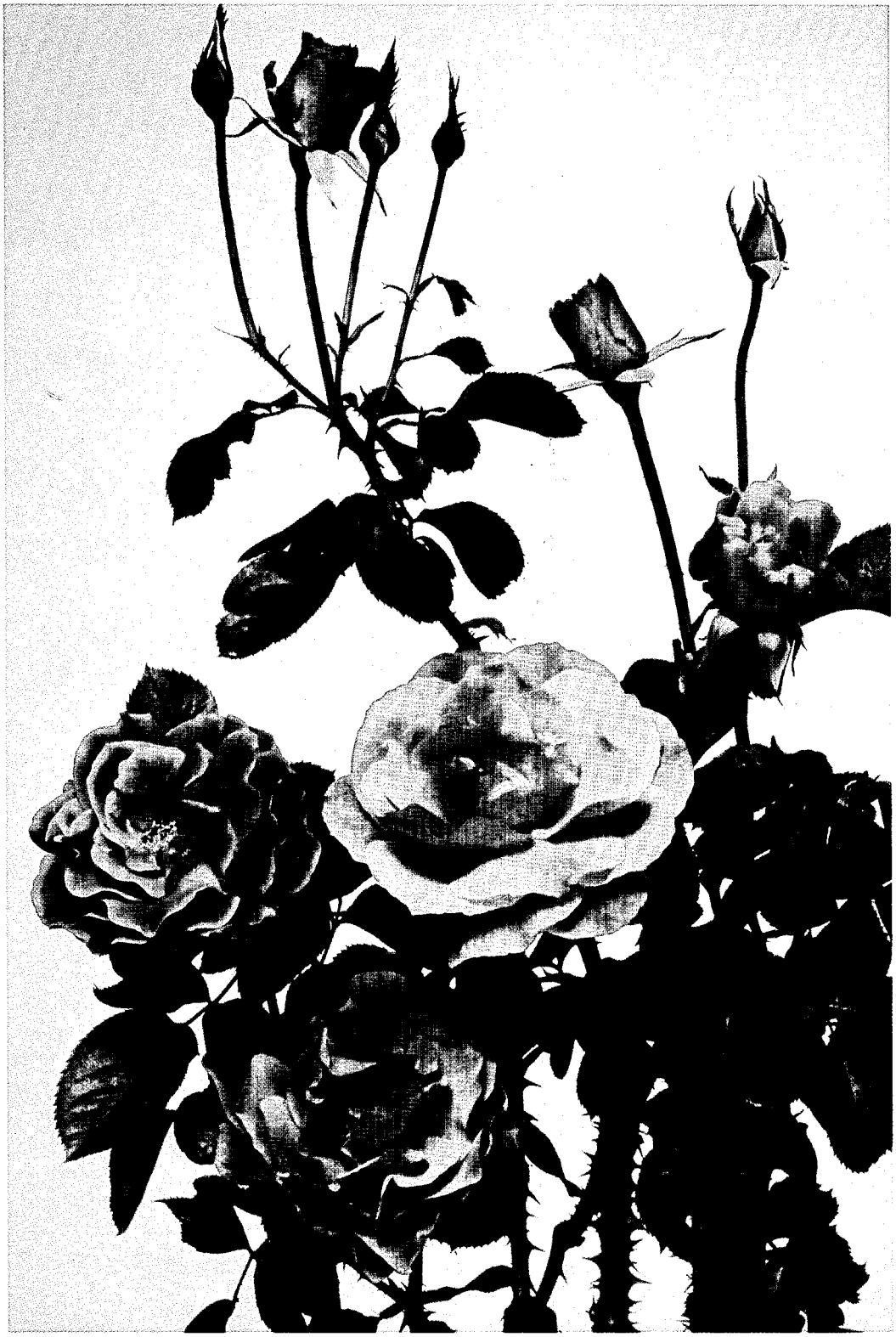

United States Patent

Plant Pat. 3,972

Patented Nov. 2, 1976

3,972

ROSE PLANT

David L. Armstrong, Orange, Calif., assignor to Armstrong Nurseries, Inc., Ontario, Calif.

Filed Nov. 18, 1975, Ser. No. 633,008

Int. Cl.[2] A01H 5/00

U.S. Cl. Plt. 20 1 Claim

ABSTRACT OF THE DISCLOSURE

A new variety of grandiflora rose of the outdoor bush type raised mainly for garden decoration. The flower petals are nearly round, and uniformly orange-red, except in the cool weather of spring and fall, at which time they are deep-maroon in color, with petals edged with vermillion. The variety has better than average resistance to mildew, as compared to similar varities raised under parallel conditions. The fully-opened blooms range from 3¾ inches to 4½ inches in diameter, and have double petalage of 32 petals and 5 to 10 petaloids regularly arranged. The plant is vigorous in growth, many-branched, with many thorns and prickles. It blooms freely outdoors and almost continuously during the growing season.

This invention relates to a grandiflora rose bred and discovered by David L. Armstrong in Ontario, Calif. Unless otherwise stated, all references to plant characteristics herein will relate to plants grown in Ontario, Calif., and references to climate will refer to the climate of that region.

The seedling had for its seed parent "Fandango," P.P. 894, and for its pollen parent "Simon Bolivar," P.P. 2,705. The new cultivar maintains its distinguishing characteristics through succeeding propagations by budding. It is primarily an outdoor rose, having a vigorous habit of growth with many thorns and prinkles on its branches and stems.

Although the new variety occasionally bears its flowers singly, they usually are grouped three or more to the stem in irregular clusters, on short to medium-length stems of normal strength. The plant blooms freely outdoors and almost continuously during the growing season. The flowers have a slight to moderate pollen fragrance.

This new cultivar differs from its seed parent, Fandango, in the characteristic deep-maroon but vermillion-edged color pattern of its petals in cool weather, whereas Fandango flowers remain uniformly orange-red until they fade; also in the shape of the petals, which are nearly round as compared to Fandango's obovate petals, and in petal count, which is from 25 to 32 petals plus 5 to 10 petaloids in contrast to Fandango's 17 to 21 petals and 3 to 5 petaloids.

The new cultivar differs from its pollen parent, Simon Bolivar, primarily in the characteristic deep-maroon but vermillion-edged petals of its cool-weather color pattern, while Simon Bolivar remains uniformly orange-red; also in that the new cultivar has flowers slightly smaller than the pollen parent and averages more than twice as many pistils per flower.

The accompanying drawing shows the development of the flower from the bud to full maturity. The center bloom shows the bloom fully and freshly opened under usual conditions. The bloom three days later is shown at the lower left. For purposes of comparison, the bloom illustrated to the extreme left of the drawing is one which opened in moderately cool weather. It shows a phase in the development of the vermillion-fringed deep-maroon petals, characteristic of spring- and fall-weather blooms.

Throughout this specification, color names beginning with a small letter signify that the name of that color, as used in common speech, is aptly descriptive. Color names beginning with a capital letter designate values based upon the Nickerson Color Fan, put out by Munsell Color Co.

BUD

The peduncle is average as to both length and caliper. It is erect and has numerous stipitate glands. The color is between Strong Yellow Green, 5GY6/8, and Strong Yellow Green, 2.5GY6/8, overlaid with near Dark Red, 2.5R3/7.

Before the calyx breaks, the bud is small to medium in size, of short to medium length, ovoid, and having foliaceous appendages and stipitate glands, on the surface of the bud. Foliaceous parts usually extend beyond the tip of the bud for a distance equal to one-fourth or more of its length.

As the calyx breaks, the color is between Dark Reddish Orange, 7.5R4/11, and Dark Red, 5R3/7. The inner surface of the sepals carries a fine, wooly tomentum. Margins of sepals which developed on the outside surface have stipitate glands, while other margins have fine, wooly tomentum. The outer surface of the sepals bears stipitate glands.

As the first petal opens, the bud is average in size, and medium length and ovoid to urn-shaped in form. The color on the outside of the petal is between Moderate Reddish Brown, 7.5R3/6, and Strong Red, 5R4/12. The inner surface of the petal is near Dark Reddish Orange, 7.5R4/11, but is more vivid. The bud opens up well, but it is retarded, and sometimes prevented from opening, by cold, or wet weather.

BLOOM

When fully open, the bloom is average in size, being from 3¾ to 4½ inches in diameter. The petalage is double, with from 25 to 32 petals, plus 5 to 10 petaloids, arranged regularly. The bloom is open to cupped at first, becoming open. The petals remain somewhat loosely cupped at first, and later, at maturity, become more loosely cupped to flat.

The petals are of medium to heavy thickness, moderately leathery, with the inside velvety and the outside slightly shiny to satiny. The shape of the outside petals is nearly round, while the intermediate and inside petals are broadly obovate. The colors may be modified by being shaded and/or washed with other colors.

The description which follows is of a flower newly opened in the month of August, and which had been grown outdoors, in Ontario, Calif.

The outer surface of the outside petal was between Strong Red, 5R4/12, and Dark Red, 5R3/7. The inner surface of the outside petal was more vivid than a color between Strong Reddish Orange, 7.5R5/13, and Dark Reddish Orange, 7.5R4/11. The outer surface of both the intermediate and the inner petals was near Strong Red, 5R4/12. The inner surface of the outer, intermediate and inner petals was the same color, namely, more vivid than a color between Strong Reddish Orange, 7.5R5/13, and Dark Reddish Orange, 7.5R4/11.

The description immediately following is of a rose that was open for three days, in the month of August, having been grown outdoors in Ontario, Calif.

Both the outside and inside petals were of the same coloration, the outer surfaces being between Strong Red, 5R4/12, and Dark Red, 5R3/7, while the inner surfaces were more vivid than a color between Strong Reddish Orange, 7.5R5/13, and Strong Red, 5R4/12.

The general color effect of the newly opened flower was more vivid than a color between Strong Reddish Orange, 7.5R5/13, and Strong Red, 5R4/12. After being three days open, the general color effect was the same as the newly opened flower, except that it was somewhat closer to the Strong Red color.

The petals drop off cleanly, except for petaloids. With cooler nights the inside surfaces of all petals (including those of the buds) tend to deepen in color to near Dark Red, 2.5R3/7, with only the margins of the petals retaining the color described just above. In very cool weather, the flowers do not open readily.

The flower on the bush in the garden persists for from four to five days, in the month of August, in the locality named. Cut roses grown outdoors and kept at living-room temperatures will last from three to four days in the month of August.

REPRODUCTIVE ORGANS

Stamens: The stamens are averag, in number, arranged regularly about the pistils, a few being mixed with petaloids.

Filaments: The filaments are of medium length, being 5 to 9 mm. in length. The color is near Brilliant Yellow, 5Y9/9, at the base, and blending to near Deep Pink, 10RP6/12, one-quarter to one-half way up the filament. Most are with anthers.

Anthers: The anthers are small and all open approximately at once. The under side is near Strong Purplish Pink, 7.5RP7/10, in color. The upper side is not readily visible, being creased along the midrib and folded laterally upward, but when visible it is the same color as the under side.

Pollen: There is a moderate amount of pollen, which is near Strong Orange Yellow, 7.5YR7/11, in color.

Pistils: The number of pistils is variable. Usually there are approximately 180, which is average to many.

Styles: Styles are uneven, from average length to long, from average to heavy caliper, and somewhat loosely bunched. The color is between Moderate Red, 2.5R4/10, and Dark Red, 2.5R3/7.

Stigma: The stigma is near Light Yellowish Pink, 2.5YR9/3, in color.

Ovaries: Most of the ovaries are enclosed in the calyx, but some protrude.

Hips: Hips are short to average length, and globular. They are smooth, and have thick, fleshy walls. The color of the immature hip is between Strong Yellow Green, 5GY6/8, and Moderate Yellow Green, 5GY5/6.

Sepals: The sepals are medium-length to long, recurved and permanent. The inside coloration (from a one-half mature hip) ranges from near Moderate Brown, 5YR3/3, to between Strong Yellow Green, 2.5GY6/8, and Moderate Yellow Green, 2.5GY5/5, overlaid with fine whitish tomentum. The outside coloration (from a one-half mature hip) is the same as the inside, but without any tomentum.

Seeds: Seeds are small in size and average in number, there being from 10 to 25.

FOLIAGE

The compound leaves usually comprise from three to seven leaflets, and are from normal to abundant in quantity, medium size to large, heavy, somewhat leathery and semi-glossy. The leaflets are ovate in shape, with apex acute to mucronate, base obtuse, and margin doubly to irregularly serrate.

The mature foliage, on its upper surface, is near Moderate Olive Green, 2.5GY4/3, while the under surface is near Moderate Yellow Green, 2.5GY5/5, overlaid with a heavy grayish bloom.

The young foliage displays a basic color on its upper surface near Moderate Olive Green, 2.5GY4/3, heavily overlaid with near Dark Red 2.5R3/7, while the under surface is near Dark Red, 2.5R3/7.

The rachis is from average to heavy in size, the upper side being grooved, and with some stipitate glands on the edges. The under side is sparsely prickly and with stipitate glands.

The stipules are medium-length to long, medium-width to wide, and with medium-length points which turn out at an angle of less than 45°.

The plant displays a more than average resistance to mildew when compared to other commercial cultivars grown under similar conditions in Ontario, Calif.

GROWTH

The plant is bushy in habit, upright-spreading, and much branched. It displays a vigorous growth. The canes are from medium to heavy in caliper.

The main stems are between Light Olive, 10Y5/5, and Light Olive 7.5Y5/5, in color. They bear very many large prickles, which are medium-length to long, almost straight to hooked slightly downward, and with medium-length; moderately broad bases. The color of these large prickles is between gray and Strong Brown, 5YR4/5. There are from few to several small prickles, the color of which is the same as that of the large prickles. There are no hairs.

The branches are between Strong Yellow Green, 5GY6/8, and Moderate Yellow Green, 5GY5/6, in color. They bear several large prickles, which are medium-length to long, and almost straight to hooked slightly downward, and with medium-length moderataly broad bases. The color of these prickles is between Brownish Orange, 5YR5/8, and Strong Brown, 2.5YR4/7. There are several small prickles, whose coloration is the same as the large prickles. There are no hairs.

The color of the new shoots is between Moderate Yellow Green, 7.5GY5/7, and Moderate Olive Green, 7.5GY4/4, overlaid with near Deep Purplish Red, 7.5-RP3/9, especially where exposed to sunlight. There are several large prickles which are medium-length to long, almost straight to hooked slightly downward, with medium-length moderately narrow bases. The color of these large prickles is near Deep Purplish Red, 7.5RP3/9. There are several small prickles, and their color is the same as that of the large prickles. There are no hairs.

I claim:

1. A grandiflora rose plant substantially as herein shown and described, said plant being distinctively characterized in that its blooms are generally orange-red but, in the cool weather of spring and fall the blooms have deep-maroon petals which are edged with vermillion, the plant being further characterized in that it has, in combination, a vigorous and many-branched habit of growth, with many large prickles on stems and branches, and further in that its foliage manifests a better than average resistance to mildew than roses of similar type grown under parallel conditions; the flowers of said rose ranging from approximately 3¾ to 4½ inches in diameter, with from approximately 25 to 32 nearly round petals, plus 5 to 10 petaloids and upwards of 180 pistils in each flower.

No references cited.

ROBERT E. BAGWILL, Primary Examiner